United States Patent [19]

Tritsch

[11] Patent Number: 4,576,598
[45] Date of Patent: Mar. 18, 1986

[54] DISPOSABLE DIAPER WITH IMPROVED ADHESIVE TAB SYSTEM

[75] Inventor: Ludwig Tritsch, Wilmette, Ill.

[73] Assignee: Personal Products Company, Milltown, N.J.

[21] Appl. No.: 545,986

[22] Filed: Oct. 27, 1983

[51] Int. Cl.[4] .............................................. A61F 13/16
[52] U.S. Cl. .................................... 604/390; 604/389
[58] Field of Search ................................ 604/389, 390

[56] References Cited

U.S. PATENT DOCUMENTS

| | | | |
|---|---|---|---|
| 3,926,191 | 12/1975 | Tritsch | 604/390 |
| 3,931,666 | 1/1976 | Karami | 604/390 |
| 3,952,744 | 4/1976 | Aldinger | 604/390 |
| 4,060,085 | 11/1977 | Karami | 604/390 |
| 4,177,812 | 12/1979 | Brown et al. | 604/390 |

*Primary Examiner*—C. Fred Rosenbaum
*Assistant Examiner*—Sherri Vinyard
*Attorney, Agent, or Firm*—Martha A. Michaels

[57] ABSTRACT

A disposable diaper having an absorbent layer and a moisture-impervious backing sheet. The diaper has an adhesive tab system comprising an adhesive tab and a release liner. The adhesive tab has an anchoring end portion which is permanently attached to the backing sheet, an intermediate portion, and a free end portion. The release liner has an end portion which is permanently secured to an outermost portion of the free end portion of the tab in covering relation in the free end portion of the adhesive tab. The intermediate portion of the adhesive tab may be folded back under the backing sheet with the tacky surface thereof facing outward of the backing sheet and the free end portion of the adhesive tab and the release liner may be further folded back such that the other surface of the release liner is in covering relation to the intermediate portion of the adhesive tab.

6 Claims, 7 Drawing Figures

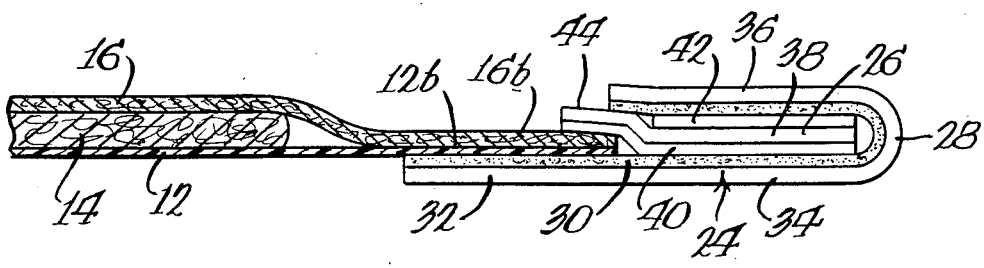
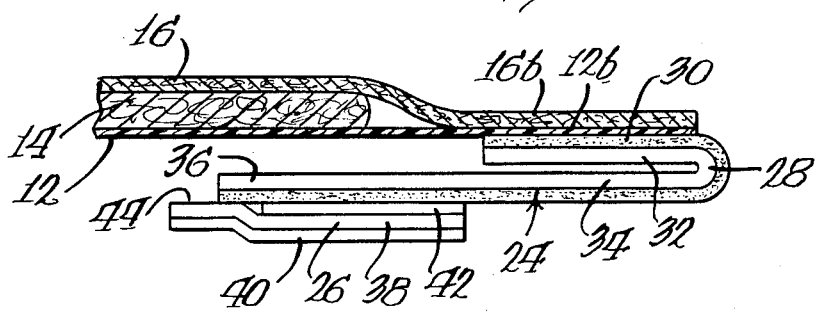
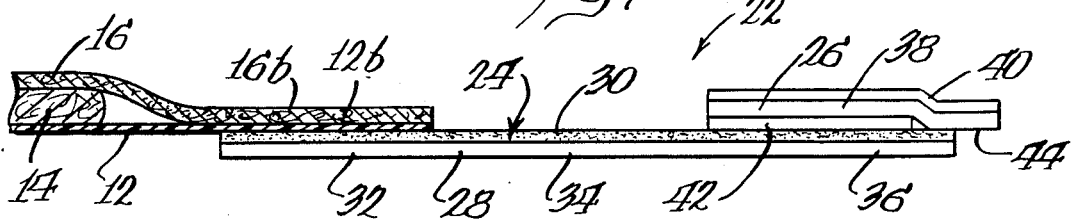
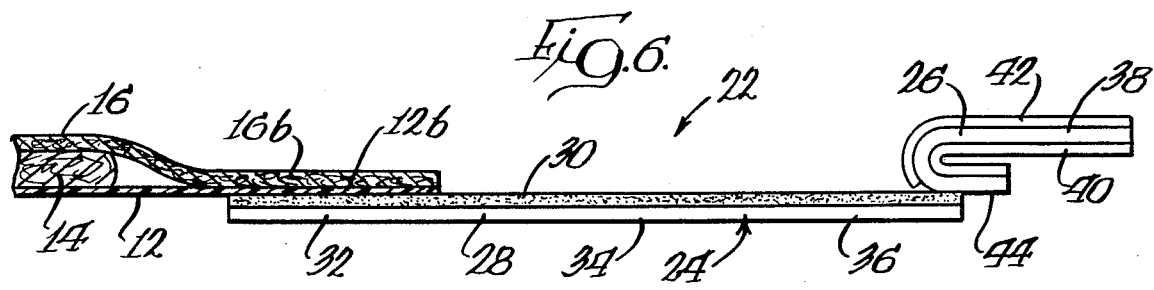

DISPOSABLE DIAPER WITH IMPROVED ADHESIVE TAB SYSTEM

TECHNICAL FIELD OF THE INVENTION

This invention relates to disposable diapers. More particularly, this invention relates to disposable diapers adapted to be secured in place by adhesive tabs.

BACKGROUND OF THE INVENTION

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet, generally made of a plastic film such as polyethylene film or the like. Typical disposable diaper structures are shown in U.S. Pat. No. 3,612,055 to Mesek et al. and in U.S. Pat. No. Re: 26,151 to Duncan et al.

As may be seen from the above-cited patents, it is desirable to obviate the problems that are inherent in closure systems which utilize extraneous fasteners such as safety pins, snaps and zippers. To this end, adhesive closure systems have presented acceptable solutions.

One of the most convenient adhesive systems that has been developed to date is the system, shown in the above-cited patents, in which adhesive tabs are adhered to the backing sheet extending outwardly from opposite sides of the diaper at one end thereof, and in which the exposed areas of the adhesive strips are provided with readily separable cover strips which protect the exposed areas until ready for use. However, disposable diapers using an adhesive closure system of this general type have the disadvantage that the consumer has to dispose of the cover strips when they are separated from the adhesive tabs. This is an inconvenience to the consumer who is placing the diaper on a baby at about the same time.

An illustrative prior art adhesive system having cover strips permanently attached to the diaper is disclosed in U.S. Pat. No. 3,646,937 to Gellert. The Gellert arrangement has the disadvantage of having a release film permanently anchored to the inside surface of the diaper, where it can possibly come into contact with a baby's tender skin. Additional disadvantages are the complexities and expense which are added to the manufacturing process by requiring each adhesive closure to be manipulated on the front side, around the edge, and on to the back side of the diaper, instead of handling the adhesive closure on one side only.

Another prior art adhesive system having cover strips permanently attached to the diaper is disclosed in my U.S. Pat. No. 3,926,191. In this arrangement one end of the releasable cover strip is permanently anchored to the outside surface of the backing sheet of the diaper and extends over the entire length of the portion of the adhesive tab which extends from the diaper. Although this adhesive tab arrangement has alleviated some of the disadvantages of the theretofore prior art adhesive closures, the length and particular location of the cover strip has proved to be inconvenient during use by the consumer. In particular, it is necessary for the consumer to make sure that the cover strip is adequately positioned away from the adhesive tab prior to urging the adhesive tab into contact with an adjacent outer surface of the diaper.

SUMMARY OF THE INVENTION

In this invention, the adhesive tab has a tacky adhesive surface which extends generally the entire length thereof in facing relationship to the backing sheet of the diaper. The adhesive tab has an anchor end portion, an intermediate portion and a free end portion. The anchoring end portion is permanently secured to an outside surface of the backing sheet at a marginal location thereof. A release liner is provided having release coatings on both surfaces thereof. The release liner has an end portion thereof which is permanently secured to an outermost portion of the free end portion of the adhesive tab such that the release coating on one of the surfaces of the release liner is releasably attached to and covers the tacky surface of the free end portion of the adhesive tab.

In its storage position, the intermediate portion of the adhesive tab is folded back under the backing sheet. The free end portion of the adhesive tab and the release liner are further folded back such that the release liner is releasably attached to and covers the tacky surface of the intermediate portion of the adhesive tab.

In accordance with a preferred form of the invention, one surface of the end portion of the release liner is not coated with a release coating and is secured to the free end portion of the adhesive tab such that it extends beyond the end thereof so as to serve as a fingerlift to unfold the adhesive tab.

BRIEF DESCRIPTION OF THE DRAWINGS

FIG. 4 is a cross-sectional view similar to FIG. 3 illustrating a step in the folding sequence of the adhesive tab;

FIG. 4A is a cross-sectional view similar to FIG. 3 illustrating an alternative step in a folding sequence of the adhesive tab;

FIG. 5 is an enlarged cross-sectional view of a portion of the diaper with the adhesive tab in its unfolded position as taken generally along line 5—5 of FIG. 1; and FIG. 6 is a cross-sectional view similar to FIG. 5 of the diaper with the release liner in its folded back position.

DETAILED DESCRIPTION OF THE INVENTION

Figure 1:
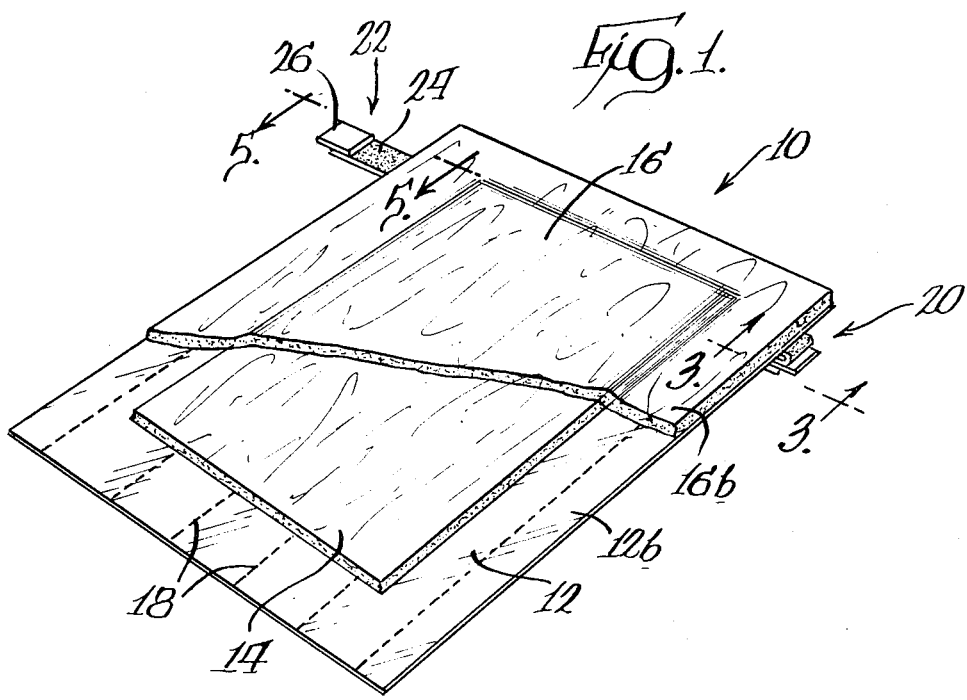
FIG. 1 is a perspective view of a disposable diaper, partially broken away, embodying adhesive tab arrangements of the invention, with one adhesive tab in a folded position and the other adhesive tab in an unfolded position.

Referring to FIG. 1 of the drawings, the diaper assembly 10 comprises a lowermost moisture-impervious backing sheet or layer 12, a highly moisture-absorbent fibrous batt of panel 14, and an overlying facing sheet or layer 16 of fibrous material, all of which are rectangular in shape. The backing layer 12 and the facing layer 16 are equal in dimension and coterminous with each other, while the absorbent batt 14 is smaller in dimension and centrally disposed with respect to the backing layer 12 and the facing layer 16. The backing layer 12 and the facing layer 16 are in contact with each other at the marginal portions of diaper 10 extending peripherally beyond the absorbent batt 14, i.e., in the portions 16b and 12b of the facing layer 16 and the backing layer 12, respectively.

In a preferred embodiment of the invention, a moisture-impervious backing sheet 12 is formed of polyethylene having a thickness of approximately 0.0001 inch. The sheet may be smooth, or may be embossed to improve its drape and feel. Other suitable flexible moisture-impervious sheets may be used in accordance with the invention such as, for example, polyethylene terephthalate sheets having a thickness of about 0.005 inch.

The absorbent batt 14 is formed of loosely compacted short cellulosic fibers, such as wood pulp fibers, or cotton linters, or mixtures thereof, which are primarily held together by interfiber bonds requiring no added adhesive, as is know in the art. Briefly, the absorbent batt 14 is a low bulk density coherent web of loosely compacted cellulose fibers preferably comminuted wood pulp fibers in the form of so-called "fluff".

Several different types of facing materials may be used for facing layer 16, for example, the facing may be a nonwoven web made of a mixture of fibers consisting predominantly of inexpensive, short, cellulosic fibers such as short wood pulp fibers or cotton linters in amounts of 75 percent to 98 percent, the balance being textile length fibers such as rayon as described in U.S. Pat. No. 3,663,348 to Liloia, et al.

Nonwoven facing materials suitable for use can have fabric weights in the range of from about 0.5 to 5 ounces per square yard and densities of less than 0.15 g/cc., generally in the range of 0.05 to about 0.1 g/cc. The dry strength of the facing sheet for a fabric having a weight of about 1.5 ounces per square yard is at least 0.15 lbs. per inch of width i the machine direction and at least 0.1 lb per inch of width in the cross direction. Such fabrics have good elongation, loft, softness, and drape characteristics. Facings may also be made of an apertured nonwoven fabric which is formed, for example, in accordance with the teachings of commonly assigned U.S. Pat. Nos. 2,862,251; 3,081,514; and 3,081,515. Furthermore, facings may also be made from other types of fabric such as those disclosed and described in U.S. Pat. No. 3,485,706 to Evans. Such facings can be made of naturally occurring fibers, synthetic fibers or blends thereof. Typical facing sheets made of polyester type fibers may have a weight of 0.75 ounces per square yard.

In addition, facings may be made from non-apertured materials such as nonwoven isotropic webs or apertured polyolefin or polyester films having the desired moisture permeability. In all of the aforementioned facings, the materials should be relatively hydrophobic so as to retard wicking within the facing.

The moisture absorbent batt or panel of a desired shape, but smaller than the facing and backing, can be formed in accordance with the teachings of U.S. Pat. No. 3,612,055 to Mesek, et al.

A suitable backing material for the disposable diapers embodying the present invention can be an opaque polyolefin; for example, polyethylene about 0.001 inch thick. Another suitable material for this purpose is polyethylene terephthalate having a thickness of about 0.005 inch.

The absorbent batt 14 is adhered to the backing layer 12 by bead lines of adhesive 18 substantially throughout the interface therebetween. Marginal portions 16b and 12b of facing layer 16 and backing layer 12, respectively, are also adhered to each other by bead lines 18. If backing layer 12 is made of a thermoplastic material, facing layer 16 and absorbent batt 14 can be attached thereto by heat bonding.

The above description of the construction of diaper 10 is only exemplary and, as is well known in the art, the specific construction of the backing layer 12, the absorbent batt 14, and the facing layer 16 may take many different forms. The adhesive tab system in accordance with the present invention is contemplated for use in combination with all such diaper constructions which are known today or which may become known in the future.

Diaper assembly 10 includes a pair of adhesive tab systems 20 and 22 which are used to secure the diaper in place on an infant. The adhesive tab systems 20 and 22 are of identical construction and, accordingly, only one tab system will be hereinbelow described, it being understood that the like numerals indicated in the drawings with respect to both systems shall indicate corresponding construction and arrangement. As seen in FIG. 1, the adhesive tab systems 20 and 22 are positioned at a pair of the adjacent corners of the marginal portions 12b.

Referring to FIG. 1 adhesive tab system 20 is shown in its unfolded or flat position and adhesive tab system 22 is shown in its folded or storage position. Adhesive tab system 20 includes an adhesive tab 24 and a release liner 26.

Referring to FIGS. 3–6, the adhesive tab 24 is an elongated tape strip 28 having a pressure-sensitive, tacky, adhesive layer 30 extending generally over the entire length thereof. Adhesive tab 24 has an anchoring end portion 32, an intermediate portion 34, and a free end portion 36, all of approximately equal length. The anchoring end portion 32 is permanently secured to the outside surface of backing layer 12 with the adhesive layer 30 in facing contact thereto.

The tape strip 28 suitable for the purposes of the invention can be made from a wide variety of materials, provided that such materials are sufficiently flexible. Illustrative material for this purpose are polyalkylene webs such as polyethylene sheet, polypropylene sheet, and the like. Other materials include treated paper, tyvek (a spun-bonded polyethylene material available from du Pont), nonwoven fabrics and other polymeric films. The adhesive layer 30 is formed by applying a coating of a pressure-sensitive adhesive composition known in the art to the tape strip 28. The applied adhesive shall have good tack, good cohesive strength, good resistance to moisture and good resistance to aging. Illustrative of such adhesive compositions are mixtures of natural or synehetic rubber, zinc oxide, and various resins, also latices of natural or synthetic rubber, or water dispersions of acrylic tacky polymers or copolymers.

Release liner 26 is a paper or plastic film material layer 38 which has suitable release coated surfaces 40 and 42 applied thereto. As seen in the figures, the release surface 42 teminates short of the marginal end of layer 38 so as to define a surface area indicated at 44. The surface area 44 does not have the release properties of the remainder of the surface area of release liner 26.

As best seen in FIG. 5, the release liner 26 is permanently secured to the free end portion 36 of adhesive tab 24 with release surface 42 in a covering relationship to the adhesive layer 30. A portion of the surface area 44 contacts the adhesive layer 30 at its outermost extremity to permanently secure the release liner 26 to the adhesive tab 24. In so doing, release liner 26 is in essence pivotally secured to the outer end of adhesive tab 24 and is movable between a flat position, as in FIG. 5, and a folded back position, as in FIG. 6. In accordance with a preferred form of the invention, the surface area 44 is approximately $\frac{1}{4}$ inch to $\frac{1}{2}$ inch wide and a portion thereof extends beyond the end of adhesive tab 24 to function as a finger-lift tab.

Figure 3:
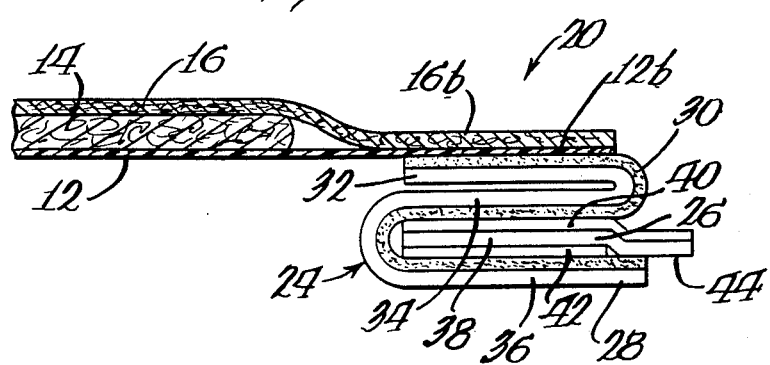
FIG. 3 is an enlarged cross-sectional view of a portion of the diaper with the adhesive tab in its folded position as taken generally along line 3—3 of FIG. 1.

Referring to FIG. 3, the adhesive tab system 20 is shown in its folded or storage position. The present invention anticipates two alternative sequences of folding steps to attain this folded position. The release liner 26 is initially secured to adhesive tab 24, which in turn is then secured to the backing 12 of diaper 10, both as shown in FIG. 5. With the tab system 20 so oriented the adhesive tab 24 is folded either as shown in FIG. 4 or as shown in FIG. 4A. Referring to FIG. 4, the free end portion 36, and the release liner 26 secured thereto, are folded up and over intermediate portion 34 such that release surface 40 of release liner 26 is in covering relationship to the tacky surface 30 of intermediate portion 34. The end portion of release liner 26 rests on top of the marginal edge of facing layer 16. The intermediate portion 34, the free end portion 36 and the release liner 26 sandwiched therebetween are then folded back under the anchor end portion 32 to attain the folded position as shown in FIG. 3. Alternatively, as seen in FIG. 4A, the free end portion 36, having the release liner 26 secured thereto, and the intermediate end portion 34 are folded back under the anchor end portion 32 and the backing layer 12. The free end portion 36, and the releaser line 26 secured thereto, are then folded back under the intermediate portion 34 such that release surface 40 of release liner 26 is in covering relationship to the tacky surface 30 of intermediate portion 34 so as to attain the folded position as shown in FIG. 3.

The adhesive tab systems 20 and 22 in their folded positions are substantially contained within the confines of the diaper 10. This facilitates the packaging of a plurality of diapers 10 in a suitable carton for ultimate use by the consumer.

Figure 2:
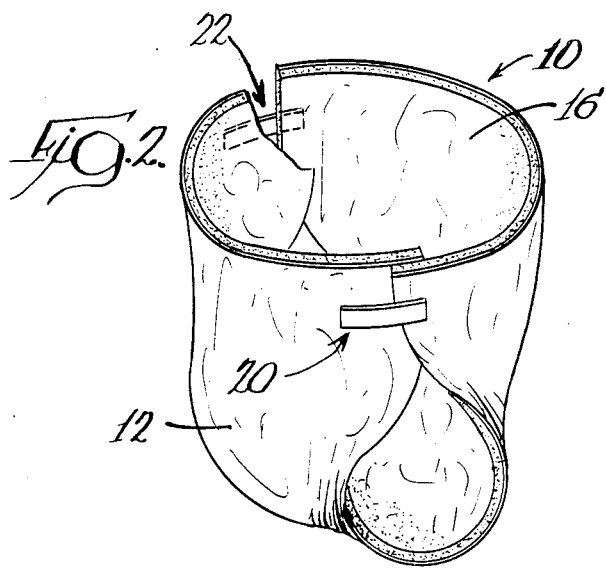
FIG. 2 is a perspective view of the diaper of FIG. 1 in the position it assumes when placed upon an infant.

In use, a diaper equipped with the adhesive fasteners of the present invention is applied to the infant by laying out the diaper on a suitable flat surface and placing the infant thereon so that the waist-underlying end of the diaper is that having the adhesive tabs. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive tab systems 20 and 22 are then prepared for use by grasping the finger lift tab portions and pulling same outwardly to unfold the adhesive tab 24 into its orientation as in FIG. 5. The inner ends of the release liner 26 are then folded back to expose the tacky surface 30 of free end portion 36 as shown in FIG. 6. The adhesive tabs 24 are then used to secure the diaper in the desired position by simply urging the pressure-sensitive tacky surfaces 30 into contact with the adjacent outer surface of the diaper, as shown in FIG. 2.

The adhesive tab system 20 of the present invention does not require the disposal of the release liner 26. The liner 26 is conveniently located out of the way when the adhesive tab 24 is unfolded for use. Further, the adhesive tab 24 is attached only to the backing layer 12 of the diaper and no part thereof is in direct contact with the infant's skin while the diaper is worn. This avoids possible skin irritation, unlike some existing systems wherein the release liners are adhered to the facing layer of the diaper. The unique manner in which the release liner 26 is secured to the adhesive tab 24 permits the entire length of the adhesive tab 24 to have a tacky surface 30 while still permitting the adhesive tab 24 to be folded and stored substantially within the confines of the diaper. These features are attained in an arrangement which comprises only one strip of adhesive tape and one piece of a two-sided coated release liner. The simplicity of this arrangement permits the assembly thereof without the use of complicated equipment.

The foregoing description and the drawing are illustrative but are not to be taken as limiting. Still other variations and modifications are possible without departing from the spirit and scope of the present invention. For example, the release liner 26 as shown in FIG. 5 may be rotated 180° about a vertical axis, secured to the end of the adhesive tab 24, and then folded back onto itself to attain a similar orientation. It is intended that this and other modifications be covered in the appended claims as all such variations and modifications are within the scope of this invention.

What is claimed is:

1. In combination with a disposable diaper having an absorbent layer and a moisture-impervious backing sheet, an improved adhesive tab system for fastening said diaper about an infant, comprising: an adhesive tab having a tacky adhesive surface extending substantially the entire length thereof in facing relationship to said backing sheet; said adhesive tab having an anchoring end portion, an intermediate portion and a free end portion; said anchoring end portion of said tab being permanently secured to an outside surface of said backing sheet at a marginal location thereof; a release liner having release surfaces on both sides thereof; one of said release liner surfaces having a portion thereof which is permanently secured to an outermost portion of said free end portion of said tab such that the remaining portions of the release surface on said one side of said release liner is releasably attached to and covers the tacky surface of said free end portion of said tab; said intermediate portion of said tab being folded back under said backing sheet with the tacky surface thereof facing outward of said backing sheet in preparation for use of said adhesive tab; and said free end portion of said tab and the release liner affixed thereto being further folded back such that the release surface on the other side of said release liner is releasably attached to and covers the tacky surface of said intermediate portion of said tab.

2. The combination in accordance with claim 1 wherein said one of the sides of said release liner has an end portion thereof which is free of said release surface and is permanently secured to the tacky surface of said free end portion of said tab.

3. The combination in accordance with claim 2 wherein said end portion of said release liner extends a short distance beyond the end of said free end portion of said adhesive tab so as to serve as a fingerlift to unfold said tab.

4. The combination in accordance with claim 2 wherein said anchoring end portion, said intermediate portion and said free end portion are generally of equal length.

5. The combination in accordance with claim 2 wherein said end portion of said release liner which is free of said release surface is approximately ¼ inch to ½ inch wide.

6. The combination as defined in claim 2 wherein said release liner includes a release coating applied to one of the sides thereof with the exception of said end portion and a release coating applied to the other side thereof generally over the entire length thereof.

* * * * *